United States Patent [19]
Castellano

[11] Patent Number: 5,354,301
[45] Date of Patent: Oct. 11, 1994

[54] HAMMER TOE OPERATION TOOL SYSTEM AND METHOD

[76] Inventor: Bradley D. Castellano, 1306 LaFaunce Way, Fort Myers, Fla. 33919

[21] Appl. No.: 33,582

[22] Filed: Mar. 19, 1993

[51] Int. Cl.⁵ .............................................. A61B 17/00
[52] U.S. Cl. ..................................... 606/103; 606/86; 7/132; 7/158
[58] Field of Search ............... 606/103, 86, 87; 7/106, 7/107, 125, 132, 133, 158, 170

[56] References Cited

U.S. PATENT DOCUMENTS

| | | |
|---|---|---|
| 1,304,620 | 5/1919 | Steinkoenig ..................... 606/103 |
| 1,639,162 | 6/1925 | Brooks . |
| 2,590,532 | 3/1952 | Haboush . |
| 2,693,798 | 11/1954 | Haboush . |
| 2,737,835 | 3/1956 | Herz . |
| 3,315,669 | 4/1967 | Rhodes . |
| 4,136,548 | 1/1979 | Dippold ............................. 7/106 |

FOREIGN PATENT DOCUMENTS 995769A 2/1983 U.S.S.R. .

Primary Examiner—Stephen C. Pellegrino
Assistant Examiner—Sonya Harris
Attorney, Agent, or Firm—Allen, Dyer, Doppelt, Franjola & Milbrath

[57] ABSTRACT

A tool system and method useful in the preparation of a surgical wire pin extending from a toe of a patient undergoing a hammer toe operation comprises a shearing tool which forms and cuts the wire pin for affixing a protective cap to the end of the pin. The protective cap is affixed using a capping tool dimensioned to receive the wire pin formed by the shearing tool. The capping tool comprises a cartridge holding a plurality of protective caps.

9 Claims, 2 Drawing Sheets

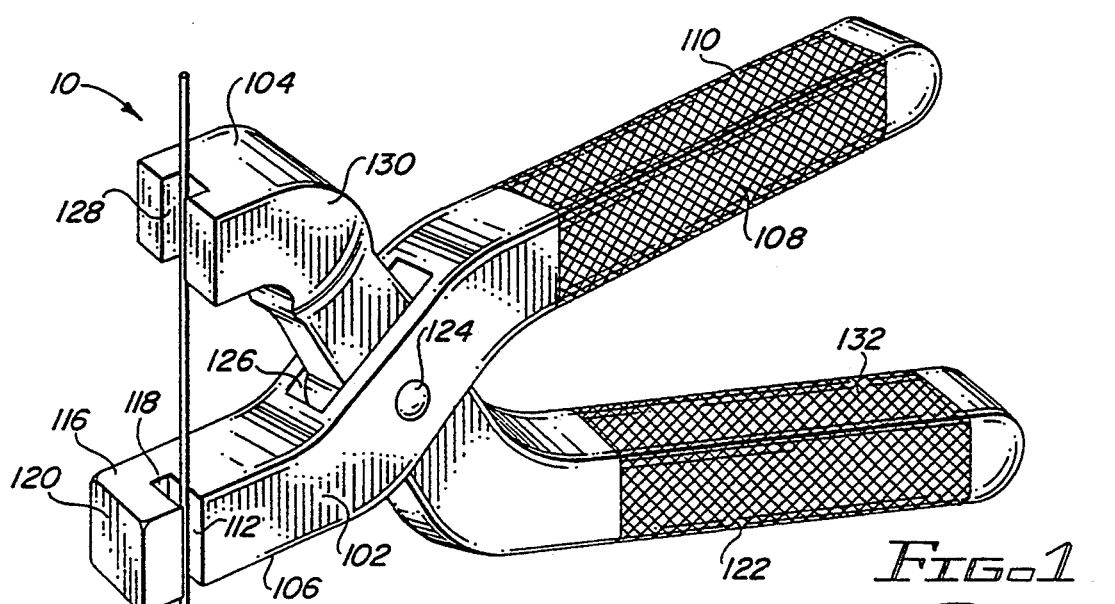
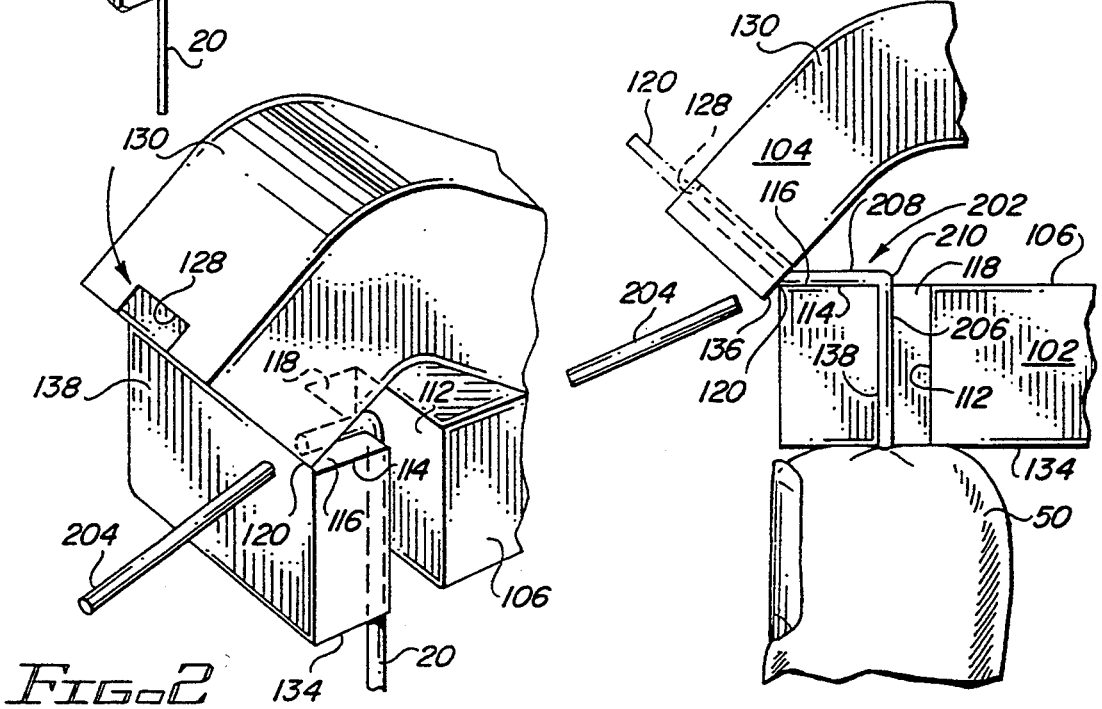
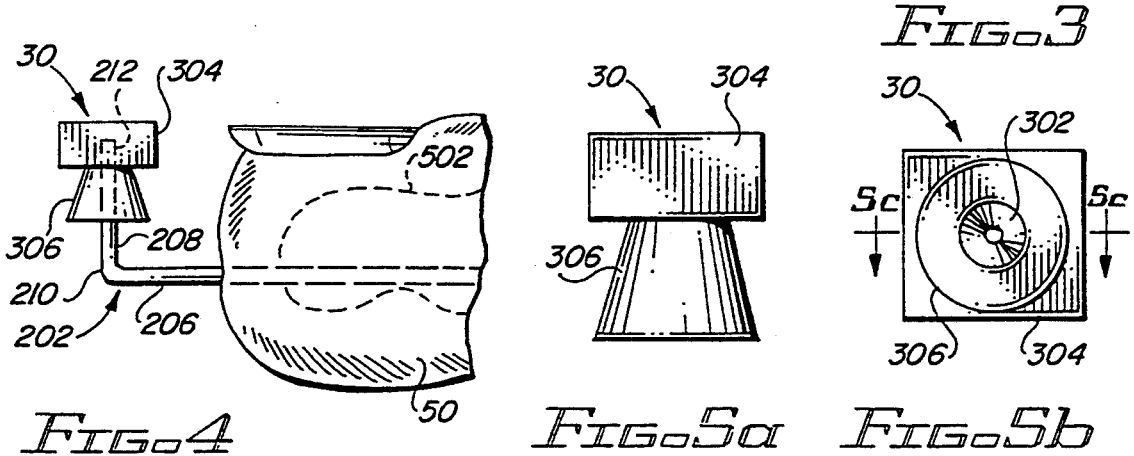

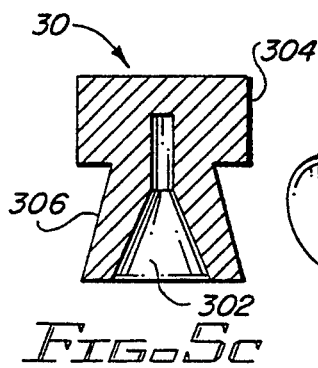
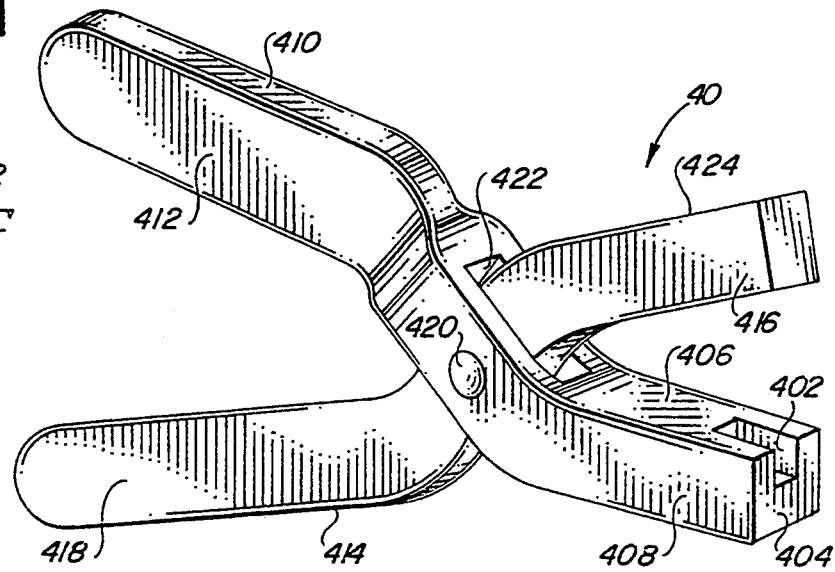
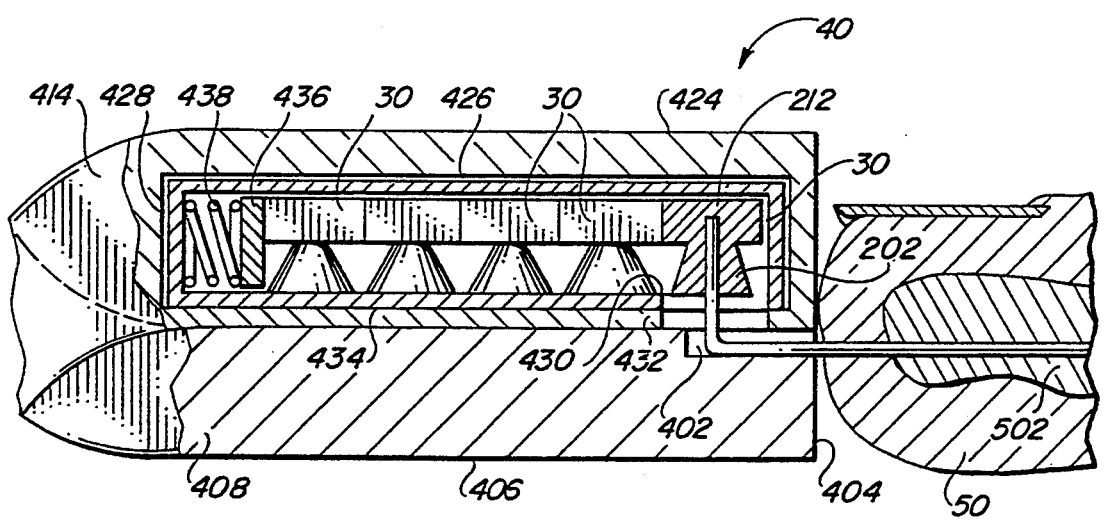

HAMMER TOE OPERATION TOOL SYSTEM AND METHOD

1. FIELD OF THE INVENTION

The invention relates generally to the preparation of surgical wire pins used in the corrective procedures of a hammer toe operation, and more particularly to the bending, shearing and capping of the bone holding surgical wire pin extending from the operative toe.

2. BACKGROUND

In podiatric surgery, it has been a problem to effectively and neatly shear and protect the surgical wire inserted through the toe and into the toe bones. The wire pin is bent to prevent migration of the pin into the toe or finger and therefore prevent the need for a surgical procedure to remove the wire pin fixation device. Typically the wire extending from the toe is cut off with a pair of end cutters. The wire is then bent to approximately a right angle using two pairs of pliers, one to hold the wire and the other to bend it. The preparation of the wire pin is necessary to protect the pin from snagging or penetrating bandages or generating puncture wounds to the patient care giver during the recovery period. A plastic cap is often used to cover the tip of the wire. The caps protect the sharp end of the exposed pin. Pins that remain unprotected can easily catch on bed sheets and may be accidentally pulled out of the digit. In addition, during the surgery, the pins are protected to prevent accidentally impaling the surgeon or assistants. Often times the wire is not cut to a uniform length or cut to a length sufficient for the efficient capping process.

Russian Patent No. 995,769 discloses a cutting forceps adapted to bend the cut end through a right angle. The cutting forceps have two hinge-joined levers. One lever has a C-shaped working jaw and the second lever has an elliptical jaw with a cutting edge. The forceps have a through canal to permit a wire pin to be placed within the canal in preparation for cutting. To cut the pin, the levers are moved apart and the long end of the pin projecting from the bone is inserted into the forceps canal. The levers are brought together under hand pressure. The cutting jaw bends and then cuts the wire pin at its tip.

SUMMARY OF INVENTION

A tool system useful in the preparation of a surgical wire pin typically protruding from a toe having undergone a hammer toe operation comprises a first tool having means for bending the wire pin at substantially a right angle. The angle bend is located a predetermined distance from the toe. Further means are provided for cutting the bent wire a predetermined distance from the angle bend. A second tool is then used in conjunction with the first tool. The second tool comprises means for receiving the bent wire pin and affixing a cap to the wire pin end. The first tool is such that the bending means and cutting means are performed with a single placement of the wire pin within the first tool. The second tool further comprises means for storing and dispensing a plurality of protective caps.

More particularly, the first tool is a shearing tool useful in the preparation of the surgical wire pin extending axially outward from a toe. The shearing tool comprises an elongated first lever arm having a proximal end and a distal end and an elongated second lever arm having a proximal end and a distal end. The second lever arm is pivotally connected to the first lever arm at a location proximate to the distal ends. A fixed jaw extends from the first lever arm distal end. The fixed jaw has a slot sized for receiving the wire pin. The slot forms a bending edge in the fixed jaw proximate to the end of the jaw. A cutting edge is formed at the end of the fixed jaw. A moveable jaw extends from the second arm distal end. The moveable jaw has a groove sized for receiving the wire pin. The moveable jaw is dimensioned to guide the wire pin over the bending edge so as to form a substantially right angle in the wire pin and guide the wire pin onto the cutting edge.

The second tool is a capping tool dimensioned to receive the surgical wire after being formed by the shearing tool. The capping tool comprises an elongated first lever arm having a proximal end and a distal end and an elongated second lever arm having a proximal end and a distal end. The second lever arm and first lever arm are pivotally connected at a location on the arms proximate to the distal ends. A fixed jaw extends from the first lever arm distal end and has a notch sized for receiving the formed surgical wire pin. A moveable jaw extending from the second lever arm distal end has means for storing the protective cap. The storing means affixed to the moveable jaw positions the cap for receipt by the end of the formed wire pin when the jaws are brought together through the action of bringing the lever arms together under pressure.

A method for the preparation of the surgical wire pin comprises the steps of providing the first tool having the fixed jaw and the moveable jaw and placing the protruding wire pin into the fixed jaws of the first tool. The wire pin is then bent at substantially a right angle by pressing the jaws together. The angle bend is located a predetermined distance from the toe based on the tool jaw dimensions. Cutting the bent wire a predetermined distance from the angle bend is accomplished through the continuing action of pressing together the jaws. The second tool is then provided for use with the first tool. The second tool comprises a fixed jaw and a moveable jaw, the fixed jaw further comprising a notch sized for receiving the bent wire pin. Storing a protective cap in the second tool moveable jaw and placing the bent wire into the notch permits the cap to be affixed to the pin end by bringing the jaws together under pressure. By storing a plurality of protective caps within the second tool permits the efficient dispensing of caps onto a plurality of formed wires.

It is the purpose of the present invention to provide for the preparation of hammer toe protruding wire pins in an effective and predetermined fashion without relying on personal judgment on the part of the care giver or surgeon preparing the wire pins. In particular, the cutting and bending of the wire pin is effectively performed with one tool and with a single placement of the protruding wire pin within the tool. The formed wire pin is then received by a second tool configured to work in cooperation with the first tooland place a protective cap onto the wire pin end in a single motion for each toe pin being capped. By forming the wire pin at a predictable angle so as to receive the cap reproducibly without error, the surgeon and patient will realize a consistent and simple procedure. In addition, by storing a plurality of caps within the second tool, a plurality of toe pins are efficiently capped.

BRIEF DESCRIPTION OF DRAWINGS

A preferred embodiment of the invention as well as alternate embodiments are described by way of example with reference to the accompanying drawings in which:

FIG. 1 is a perspective view of the present cutting tool concerned with the bending of the wire pin and shearing to a predefined length for capping;

FIG. 2 is a partial perspective view of the jaw ends of the tool in FIG. 1 illustrating the bending and shearing of the wire pin;

FIG. 3 is a side view of the cutting tool of FIG. 2 illustrating the bending edge and shearing edge of the wire pin extending from a toe;

FIG. 4 is a partial view of the cap affixed to a formed wire pin installed by the tools of the current invention.

FIG. 5a, 5b and 5c are partial front, top and cross-sectional views respectively of the cap used in the preferred embodiment;

FIG. 6 is a perspective view of the capping tool; and

FIG. 7 is a partial cross-sectional view of the preferred embodiment of the capping tool in FIG. 4 illustrating a plurality of caps contained in a cartridge;

DETAILED DESCRIPTION OF PREFERRED EMBODIMENT

In the preferred embodiment of the invention, a shearing tool 10 is used to form a surgical wire pin 20 for placement of a protective cap 30 thereon by a capping tool 40. In the preferred embodiment, the shearing tool 10 and the capping tool 40 are used in support of a hammer toe operation where the surgical wire pin 20 has been placed into and protrudes from a toe 50.

With reference to FIG. 1, illustrating the preferred embodiment of the shearing tool 10, the surgical wire pin 20 is placed within the fixed 102 and moveable 104 jaws of the tool 10. The fixed jaw 102 is located at a distal end 106 of an elongated first lever arm 108 having a proximal end 110 which forms part of a handle for the tool 10. The fixed jaw 102 comprises a slot 112 located proximate to but a defined distance 114 from the end of the jaw 102. The slot 112 and top portion 116 form a bending edge 118 further illustrated in FIG. 2. A cutting edge 120 is formed on the top portion 116 at the end of the jaw 102. With reference to FIG. 3, it is seen that the separation between the bending edge 118 and the cutting edge 120 defines the distance 114 predetermined for use with the capping tool 40 as seen in FIG. 6.

Referring again to FIG. 1, an elongated second lever arm 122 is pivotally connected to the first lever arm 108 using a pivot pin 124 passing through pivot holes in the first 108 and second 122 lever arms. As is well known in the art the pivot hole in the preferred embodiment is located proximate to the arm distal ends for an optimum mechanical advantage. In the preferred embodiment, a jaw channel 126 is formed in the first lever arm 108 and the second lever arm 122 is dimensioned to pass through the channel 126 proximate to the pivot pin 124. In this way, the lever arms can be constructed in a single plane for alignment of their respective jaws. It is appreciated that alternative pivotal connections will be used by those skilled in the art.

The moveable jaw 104 is formed with a groove 128 at the distal end 130 of the second lever arm 122. The groove 128 is sized to loosely guide the wire pin 20 when placed within the groove 128 and the jaws of the tool 10 are brought together by placing pressure on the first lever arm proximal end 10 and a second lever proximal end 132. With the wire pin 20 passing within the slot 12 and groove 128 as illustrated in FIG. 1, the jaws 102 and 104 are brought together by bringing the lever arm proximal ends 110 and 132 together under hand pressure. As illustrated in FIG. 3, the slot 12 of the fixed jaw 102 embraces the wire pin 20 while positioning the toe 50 against the bottom 134. As the moveable jaw 104 is brought toward the fixed jaw 102, the groove 128 slides along the wire pin 20 and guides the pin 20 over the bending edge 118. As pressure continues to be applied to the proximal ends, the moveable jaw 104 forces the wire pin 20 to be passed over the cutting edge 120. By biasing the pin 20 between a bottom surface 136 of the moveable jaw 104 and the cutting edge 120, the surgical wire pin 20 is sheared. With a pre-established distance 114 between the cutting 120 and bending 118 edges, the pin 20 is bent and sheared for receipt by the capping tool 40.

Referring again to FIG. 3, the wire pin 20 is made into a formed pin 202 by the bending and cutting action of the shearing tool 10. The dimensions of the formed pin 202 are established by the edge to edge distance 114 and a thickness 138 of the fixed jaw 102, remembering that in the preferred embodiment, the bottom 134 of the fixed jaw 102 is placed against the toe 50 prior to the bending action of the tool 10. The action of the tool is such to remove excess cut wire 204 and create a horizontal section 206 extending from the toe 50 and a vertical section 208 extending upward from a right angle 210, the sections having dimensions sufficient to cooperate with the capping tool 40.

It is an objective of the capping tool 40 to affix the cap 30 to the formed pin end 212 and prepare the pinned toe 50 as illustrated in FIG. 4 illustrating the toe 50 comprising the cap 30 affixed to the formed wire pin end 212. FIG. 5 illustrates various views of the protective cap 30 used in the preferred embodiment of the invention. As illustrated in FIG. 5, the cap 30 comprises a center bore 302. The bore 302 is dimensioned to tightly receive the formed wire pin 202 and has a slight cone shape to allow for an error in any pin angle 210. The square shape cap top 304 reduces motion of the cap 30 in the cartridge 428. It is anticipated that those skilled in the art will form caps 30 of varying materials such that one embodiment of the cap will receive the pin 202 while at the same time forming a bore 302. It is also anticipated that various shapes will be devised for the protective cap 30. In the preferred embodiment, the cap 30 comprises a top 304 affixed to a base 306. The bore 302 penetrates through the base 316 and partially into the top 304 leaving sufficient cap material above the pin end 212 and the surface of the top 304 to prevent the pin end 212 from protruding through the cap top 304 throughout the care giving process for the patient.

The capping tool 40 is used to affix the protective cap 30 to the sheared end 210 of the formed surgical wire pin With reference to FIG. 6, illustrating the preferred embodiment of the capping tool 40, a notch 402 is formed at an end face 404 of a fixed jaw 406. The notch 402 is dimensioned to receive the formed wire pin 202 such that the angled 210 sections 206 and 208 are loosely cradled within the notch 402. The fixed jaw 406 is affixed at a distal end 408 of an elongated first lever arm 410. The lever arm 410 comprises a proximal end 412 which forms part of a handle for the tool 40. A second elongated lever arm 414 comprises a distal end 416 and a proximal end 418. The first lever arm 410 is pivotally attached to the second lever arm 414 proximate to the distal ends 408 and 416 as described above for the shearing tool 10. The second lever proximal end cooperates with the first lever proximal end 412 to form the tool handle. Also as described earlier for the shearing tool 10, the elongated lever arms 410 and 414 are pivotally affixed using a pivot pin 420 and jaw channel 422 arrangement similar to that described for the shearing tool The capping tool 40 comprises a moveable jaw 424 affixed at the second lever arm distal end 416. With reference to FIG. 7, it can be seen that the protective caps 30 are stored within a cavity 426 of the moveable jaw 424. In the preferred embodiment, the cavity 426 is dimensioned to receive a cartridge 428 capable of holding five protective caps 30 arranged to be dispensed from an opening 430 within the cartridge 428. The cartridge opening 430 is aligned with an opening 432 in the moveable jaw bottom surface 434.

It is anticipated that one skilled in the art will devise alternate cartridge 428 designs and alternate designs for storing the cartridge 428 within the moveable jaw 424. Again with reference to FIG. 7, the preferred embodiment comprises a 436 biased against the caps 30 through the use of a compressed spring 438. The caps 30 are held in a queue within the cartridge 428 and dispensed one by one as the capping tool 40 is used.

Again with reference to FIG. 7, it can be seen that by placing the formed pin 202 within the notch 402 and closing the moveable jaw 424 onto the fixed jaw 406 by the action of bringing pressure to the handle or proximal ends 412 and of the lever arms 410 and 414, the pin end 212 is forced to penetrate the cap 30 and become affixed thereto. As discussed earlier, the cap 30 comprises a bore 302 in the preferred embodiment that snugly holds the cap 30 onto the pin end The dimensions of the notch 402 are such that they compliment the dimensions of the formed pin 202.

While a specific embodiment of the invention has been described in detail herein above, it is to be understood that various modifications may be made from the specific details described herein above without departing from the spirit and scope of the invention as set forth in the appended claims.

What is claimed is:

1. A tool system useful in forming a surgical wire pin protruding from a toe having undergone a hammer toe operation, the tool system comprising:
   a first tool for forming a wire pin for receiving a cap, the wire pin has a proximal end and a distal end, the proximal end protruding from a toe further comprising:
      means for bending the wire pin at substantially a right angle for forming an angle bend located a first predetermined distance from the toe; and
      means for cutting the bent wire pin at the distal end a second predetermined distance from the angle bend, the predetermined distances dimensioned for cooperating with a second tool for capping the wire distal end; and
   a second tool dimensioned for receiving the formed wire and for affixing a cap to the cut wire distal end, the second tool for use with the first tool, the second tool further comprising:
   means for receiving the bent wire pin; and
   means for affixing a cap to the wire pin distal end.

2. The tool system as recited in claim 1, wherein the bending means and cutting means accomodate a single placement of the wire pin within the first tool.

3. The tool system as recited in claim 1, wherein the second tool cap affixing means comprises means for storing and dispensing a plurality of protective caps.

4. A tool system useful in preparing a surgical wire pin extending axially outward from a toe, the tool system comprising:
   a shearing tool for dimensioning a surgical wire pin for receiving a protective cap, the shearing tool comprising:
      an elongated first lever arm having a proximal end and a distal end;
      an elongated second lever arm having a proximal end and a distal end, the second lever arm pivotally connected to the first lever arm at a location proximate to the distal ends;
      a fixed jaw extending from the first lever arm distal end, the fixed jaw having a slot sized for receiving the wire pin, the fixed jaw further having a bending edge proximate to an end of the jaw;
      a cutting edge formed at the end of the fixed jaw; and
      a movable jaw extending from the second arm distal end, the moveable jaw having a groove sized for receiving the wire pin, the moveable jaw dimensioned to guide the wire pin over the bending edge so as to form
   a substantially right angle in the wire pin and guide the wire pin onto the cutting edge; and
   a capping tool dimensioned to receive a surgical wire pin formed by the shearing tool and affixing a protective cap thereto, the capping tool comprising:
      an elongated first lever arm having a proximal end and a distal end;
      an elongated second lever arm having a proximal end and a distal end, the second lever arm pivotally connected to the first lever arm at a location proximate to the distal ends;
      a fixed jaw extending from the first lever arm distal end, the fixed jaw having a notch sized for receiving the formed surgical wire pin;
      a movable jaw extending from the second lever arm distal end; and
      means for storing at least one protective cap, the storing means affixed to the moveable jaw so as to position the cap for receiving an end of the formed wire pin when the jaws are brought together through the action of bringing the lever arms together under pressure.

5. The tool system as recited in claim 4, wherein the storing means further comprises:
   a cartridge dimensioned to be affixed to the moveable jaw, the cartridge sized to receive and hold five protective caps; and
   means for sequentially positioning the caps within the cartridge for being received by each formed wire pin when the moveable jaw is closed onto the fixed jaw.

6. A method for preparing and capping of a surgical wire pin protruding from a toe having undergone a hammer toe operation, the method comprising the steps of:
   providing a first tool for forming a wire pin, the first tool having a fixed jaw and moveable jaw, the fixed jaw having a slot for receiving a wire pin;
   placing the wire pin protruding from a toe into the fixed jaw of the first tool;
   pressing the jaws together for bending the wire pin at substantially a right angle thereby forming an angle bend, the angle bend located a first predetermined distance from the toe; and cuting the bent wire pin a second predetermined distance from the angle bend through a continued action of pressing together the jaws;

providing a second tool for use with the first tool, the second tool comprising a fixed jaw and a moveable jaw, the fixed jaw further comprising a notch sized to receive the bent wire pin;

providing a protective cap;

storing the protective cap in the second tools moveable jaw, the moveable jaw having means for storing and dispensing at least one cap;

placing the bent wire into the notch;

bringing the jaws together under pressure; and affixing one protective cap to an end of the wire pin.

7. The method as recited in claim 6 wherein the storing step further comprises the steps of storing a plurality of protective caps and sequentially dispensing the caps into a position for affixing the caps to each formed wire pin end.

8. A method useful in preparing and capping a surgical wire pin extending axially outward from a toe following a hammer toe operation, the method comprising the steps of:

providing a first tool having an elongated first lever arm, the arm having a proximal end and a distal end;

pivotally affixing an elongated second lever arm having proximal and distal ends to the first lever arm at a location proximate to then distal ends;

extending a fixed jaw from the first lever arm distal end the fixed jaw having top and bottom surfaces;

providing a slot proximate an end of the fixed jaw, the slot sized for receiving the wire pin, the slot providing a bending edge at a top surface of the fixed jaw proximate to the end of the fixed jaw;

forming a cutting edge at the top end of the fixed jaw; and extending a moveable jaw from the second arm distal end the movable jaw having top and bottom surfaces, the movable jaw having a cavity for storing and dispensing at least one cap;

providing a groove at an end face of the moveable jaw and sizing the groove for receiving the wire pin, dimensioning the moveable jaw to guide the wire pin over the bending edge;

placing the wire pin into the slot;

placing the wire pin into the groove;

positioning the fixed jaw bottom surface against the toe;

bringing the jaws together under pressure by closing the lever arms toward each other to bend the wire pin at a substantially right angle as the groove guides the wire pin over the bending edge; biasing the moveable jaw bottom surface against the cutting edge, the wire pin being placed therebetween; and thereafter cutting the wire pin thereby providing a formed surgical wire pin prepared for capping;

providing an elongated first lever arm having a proximal end and a distal end;

pivotally affixing an elongated second lever arm having proximal and distal ends to the first lever arm at a location proximate to their distal ends;

extending a fixed jaw from the first lever arm distal end;

providing a notchat the end of the fixed jaw sized for receiving the formed surgical wire pin;

extending a moveable jaw from the second lever arm distal end;

storing the protective cap proximate to the moveable jaw end;

positioning the cap for receiving the end of the formed wire pin;

bringing the jaws together through the action of bringing the lever arms together under pressure; and affixing the protective cap to the formed wire pin end thereby preparing the surgical wire pin for safely remaining within the toe during healing.

9. The method as recited in claim 8, wherein storing the protective cap further comprises the steps of:

providing a cartridge within the movable jaw cavity for storing and dispensing a plurality of protective caps;

positioning at least one cap for receiving the wire pin end when the jaws are brought together; and sequentially positioning a next cap into position for receiving a next wire pin end until each of the plurality of caps has been dispensed.

* * * * *